United States Patent [19]

Gerace et al.

[11] Patent Number: 5,391,590
[45] Date of Patent: Feb. 21, 1995

[54] INJECTABLE INTRAOCULAR LENS COMPOSITIONS AND PRECURSORS THEREOF

[75] Inventors: John D. Gerace, Laguna Niguel; F. Richard Christ, Laguna Beach, both of Calif.

[73] Assignee: Allergan, Inc., Irvine, Calif.

[21] Appl. No.: 3,371

[22] Filed: Jan. 12, 1993

[51] Int. Cl.⁶ .................. A61F 2/16; C08L 83/05; C08K 3/10
[52] U.S. Cl. ........................ 523/107; 623/6; 524/506; 524/862; 525/100; 525/903; 525/937; 528/15; 528/31
[58] Field of Search ............. 523/107; 623/6; 528/15, 528/31; 525/100, 903, 937; 524/506, 862

[56] References Cited

U.S. PATENT DOCUMENTS

| | | | |
|---|---|---|---|
| 3,284,406 | 11/1966 | Nelson | 528/31 |
| 3,341,490 | 9/1967 | Burdick | 523/212 |
| 3,457,214 | 7/1969 | Modic | 524/863 |
| 3,677,981 | 7/1972 | Wada et al. | 528/31 |
| 3,992,355 | 11/1976 | Itoh et al. | 526/279 |
| 3,996,187 | 12/1976 | Travnicek | 528/15 |
| 3,996,189 | 12/1976 | Travnicek | 528/15 |
| 4,122,246 | 10/1978 | Sierawski | 528/15 |
| 4,380,643 | 4/1983 | Yoshida et al. | 548/260 |
| 4,418,165 | 11/1983 | Polmanteer et al. | 523/107 |
| 4,535,141 | 8/1985 | Kroupa | 528/15 |
| 4,542,542 | 9/1985 | Wright | 623/6 |
| 4,573,998 | 3/1986 | Mazzocco | 623/6 |
| 4,608,050 | 8/1986 | Wright et al. | 623/6 |
| 4,615,702 | 10/1986 | Koziol et al. | 623/6 |
| 4,647,282 | 3/1987 | Fedorov et al. | 623/4 |
| 4,714,739 | 12/1987 | Arkles | 525/105 |
| 4,720,521 | 1/1988 | Spielvogel et al. | 528/31 |
| 4,737,558 | 4/1988 | Falcetta et al. | 526/279 |
| 4,785,047 | 11/1988 | Jensen | 524/714 |
| 4,801,642 | 1/1989 | Janik et al. | 528/15 |
| 4,868,151 | 9/1989 | Reich et al. | 525/479 |
| 4,882,398 | 11/1989 | Mbah | 528/15 |
| 4,973,642 | 11/1990 | Donatelli et al. | 528/15 |
| 4,990,560 | 2/1991 | Ikeno et al. | 524/731 |
| 5,077,335 | 12/1991 | Schwabe et al. | 523/107 |
| 5,116,369 | 5/1992 | Kushibiki et al. | 623/6 |
| 5,145,932 | 9/1992 | Sasaki et al. | 528/31 |
| 5,254,644 | 10/1993 | Kobori et al. | 528/31 |

FOREIGN PATENT DOCUMENTS 1273144 8/1990 Canada.
0110537 6/1984 European Pat. Off..

OTHER PUBLICATIONS

Parel et al, "Phaco-Ersatz: cataract surgery designed to preserve accommodation", Graefe's Arch Clin Exp Ophthalmol (1986) 224:165–173.

O. Nishi, "Refilling the lens of the rabbit eye after intercapsular cataract surgery using an endocapsular balloon and an anterior capsule suturing technique", J. Cataract Refract Surg—vol. 15, Jul. 1989.

(List continued on next page.)

Primary Examiner—Paul R. Michl
Assistant Examiner—Andrew E. C. Merriam
Attorney, Agent, or Firm—Frank J. Uxa, Jr.; Gordon L. Peterson

[57] ABSTRACT

New compositions useful as the optics of intraocular lenses, in particular injectable intraocular lenses, are disclosed. In one embodiment, such compositions comprise polymer mixtures derived from the polymerization, for example, cross-linking, of curable components in precursor mixtures. These precursor mixtures comprise curable component comprising: (A) an unsaturation functional (vinyl group-containing) polyorganosiloxane component, (B) an organosilicon component including silicon-bonded hydride groups which react with the unsaturation functional groups included in (A) during the polymerization, and (C) an effective amount of a platinum group metal-containing catalyst component; and a polymer component which is substantially non-functional. The viscosity of the polymer component is greater than the viscosity of the curable component.

15 Claims, No Drawings

OTHER PUBLICATIONS

Haefliger et al, "Accommodation of a Endocapsular Silicone Lens (Phaco-Ersatz) in the Nonhuman Primate", Ophthalmology May 1987, vol. 94, No. 5, pp. 471–477.

Saam, Formation of Linear Siloxane Polymers, 1990 American Chemical Society, pp. 71–89.

Fish et al, Ring Opening Polymerization of Cyclotetrasiloxanes with Large Substituents, pp. 36–37, Polymer Reprints, 31(1), Apr. 1990.

Boutevin et al, Synthesis of Fluorinated Polysiloxanes. 8. Properties at Low and High Temperatures of Polysiloxanes with Fluronated Graft Macromolecules, vol. 24, (3), pp. 629–632 (Feb. 4, 1991).

Grigoras, Substituted Polysiloxane Polymers: Conformation of the Pendant Groups, Polymer Preprints 31(1), 697 (1990).

Rasoul et al, Thermal and Rheological Properties of Alkyl-Substitute Polysiloxanes, 1990 American Chemical Society, pp. 91–96.

Zapf et al, Synthesis and Properties of New UV-Curable Silicones With High Refractive Index, Polymeric Prints 30(2), p. 107 (1989).

Grigoras et al, Conformational Analysis of Substituted Polysiloxane polymers, 1990 American Chemical Society, pp. 125–144.

INJECTABLE INTRAOCULAR LENS COMPOSITIONS AND PRECURSORS THEREOF

BACKGROUND OF THE INVENTION

The present invention relates to compositions useful as materials for the optics of intraocular lenses (IOLs) and to precursors of such compositions. More particularly, the invention relates to polymer mixtures which are derived from the polymerization of a portion of precursor fluids or formulations and are useful in the optics of IOLs, preferably injectable IOLs. Methods of forming IOLs are also disclosed.

Silicone polymers are known materials and many are produced using platinum-containing catalysts, which catalysts remain a part of the final product. For example, certain such silicone polymers are known to be useful in the production of IOLs. Also, curable fluid, for example, liquid, formulations including monomers which can be cured or cross-linked in the presence of platinum-containing catalysts to form silicone polymers have been suggested for use in forming a solid, transparent synthetic lens upon being injected into the lens capsule of an eye from which the natural lens has been removed. See Wright et al U.S. Pat. No. 4,608,050. Lenses which are formed in the lens capsule of the eye are generally referred to herein as injectable IOLs.

Soft, fast curing, low temperature vulcanization (LTV) silicone gels have been developed that target the physical properties of young human lenses, that is the natural lenses present in human eyes. Such soft, fast curing LTV silicone gels provide injectable IOLs that may potentially accommodate under physiological response.

Precursor fluids of such soft, fast curing LTV silicone gels can be injected to fill the natural capsular bag or a synthetic capsular bag and then solidify or cure (polymerize) in situ to form an injectable IOL. Typically, high molecular weight, high viscosity precursor fluids are used so that the material does not readily leak out of the injection sight while in its fluid state. However, with high molecular weight, high viscosity precursor silicone fluids, injection into the eye can be somewhat difficult. Also, a very low level of cross-link density is required with such high viscosity precursor fluids to achieve a similar stiffness (elastic modulus) as a young human natural crystalline lens. Unfortunately, when cross-link density is reduced, the material becomes "gummy" and non-resilient. Thus, such high molecular weight, high viscosity precursor fluids cannot be used for injectable IOLs which match or resemble the properties of a young human lens.

On the other hand, low viscosity, that is a viscosity of less than about 1000 centipoise, low molecular weight precursor fluids result in polymeric materials that are lightly cross-linked and form resilient, responsive gels, that is gels which recover from deformation very quickly. In fact, such gels can have properties quite similar to the properties of a natural crystalline lens. In addition, these low molecular weight precursors, for example, silicones, are more easily purified to achieve medical grade purity than are the higher molecular weight precursors. Also, such low viscosity precursor fluids do not require excessive pressures for injection. Thus, such precursor fluids can be injected through a hand held syringe.

While low viscosity silicone precursor fluids have desirable properties for use in forming injectable IOLs, they do have some important limitations. The most significant limitation is that, because of their fluidic consistency, such low viscosity fluids readily leak out of the desired injection sight. This limitation has been overcome by implementing a "pre-cure" process where the polymerization or cross-linking reaction is initiated prior to injection. In this manner, the fluid material thickens to a controllable viscosity and is then injected. However, there are two fundamental problems with this technique. First, the shear stresses encountered while injecting the "pre-cured" material through a small cannula result in rough areas in the final polymer which are detrimental to the functioning of the resulting lens. Also, in applications where a very fast curing gel is required, the pre-cure cycle limits the work time available for injection.

There is a continuing need for new injectable IOL materials.

SUMMARY OF THE INVENTION

New compositions, preferably useful as the optics of injectable IOLs, and precursors thereof have been discovered. Such compositions and precursors provide solutions to the problems of using low viscosity precursor fluids to form injectable IOL materials. The present invention is based, at least in part, on the finding that low viscosity fluids can be "thickened" without implementing a pre-cure cycle. The viscosity of the precursor fluid is maintained at a level so that the risk of fluid leaking is reduced. The final product is preferably soft and resilient, making it very useful as a material for an injectable IOL, for example, an injectable IOL which more preferably accommodates under physiological response. The present compositions are often suitable for any application where a liquid is injected and cures in situ to form a gel or solid.

In one embodiment, a precursor composition is formulated so that the viscosity of a low molecular weight polymerizable or curable component is increased by combining this component with a substantially non-functional, higher viscosity polymer component. During polymerization, for example, cross-linking, of the curable component, the cross-link density is increased, preferably to the point where the resulting cross-linked polymer material immobilizes or entraps at least a portion of the substantially non-functional polymer component. The cross-linked polymer material preferably has sufficient cross-link density so that the final composition or polymer mixture is soft and resilient, for example, so as to be useful as an injectable IOL material. In a particularly useful embodiment, the cross-linked polymer material of the present composition has the same resiliency and an increased cross-link density relative to a polymer composition made from the curable component without the substantially non-functional, higher viscosity polymer component being present. In other words, at comparable resiliency, the cross-linked polymer material of the present composition has increased cross-link density relative to compositions derived solely from low viscosity precursors.

Without wishing to limit the invention to any particular theory of operation, the cross-linked polymer material may be envisioned as forming cages in which is located the substantially non-functional polymer component. Regardless of its specific structure, the final composition or polymer mixture has advantageous physical (mechanical) and/or optical properties, preferably is a soft and resilient material, and more preferably is quite similar to the heterogenous natural, crystalline lens present in the eye, for example, of young human beings.

The present polymer mixtures can be used for injectable IOLs, and, in any application where injection viscosity and material resiliency are important considerations.

DETAILED DESCRIPTION OF THE INVENTION

This invention relates to polymer mixtures, precursor formulations, preferably fast curing precursor formulations, to provide such polymer mixtures, IOLs, preferably injectable IOLs, and methods of forming such IOLs. These compositions or polymer mixtures are derived from polymerization, preferably including cross-linking, of a polymerizable or curable component in a mixture comprising the polymerizable or curable component and a polymer component. The polymer component is substantially non-functional and has a viscosity which is greater, preferably at least about 50 times greater, than the viscosity of the curable component. In general, the curable component and polymer component are each present in the present mixtures in amounts effective to provide the mixtures with a desired, preferably predetermined, viscosity and/or to provide final compositions or polymer mixtures with desired, preferably predetermined, physical and/or optical properties. The final compositions or polymer mixtures are preferably optically clear, and are useful in the optics of IOLs, for example, injectable IOLs.

The presently useful polymerizable or curable components comprise (A) an unsaturation, preferably carbon-carbon unsaturation and more preferably vinyl-containing, functional polyorganosiloxane component; (B) an organosilicon component including silicon-bonded hydride groups which react with the unsaturation functional groups included in (A) during the polymerization or curing of the curable component; and (C) a platinum group metal-containing catalyst component in an amount effective to promote the polymerization of the curable component. As noted above, the viscosity of the curable component is less than the viscosity of the polymer component. Such curable components preferably have a viscosity at least about 100 centipoise and less than about 5000 or less than about 2000, more preferably less than about 1000, centipoise. All viscosities set forth herein are measured at 250° C. unless otherwise expressly stated.

The curable component is preferably present in an amount effective to form cross-linked polymer material upon polymerization. This cross-linked polymer material preferably immobilizes or entraps, for example, physically entraps and/or otherwise immobilizes, at least a portion, more preferably at least a major portion and still more preferably substantially all, of the polymer component in the polymer mixture. The polymer component is immobilized in that it is prevented from flowing as a fluid in the final polymer mixture at normal use conditions. In one embodiment, the curable component has a chemical make-up and is present in an amount effective to form cross-linked polymer material upon the polymerization of the curable component with sufficient cross-link density so that the final composition is soft and resilient, preferably sufficiently soft and resilient to be useful as an injectable IOL. Such cross-link density is preferably increased relative to a polymer composition of comparable softness and resiliency derived solely from low viscosity precursors.

Component (A) of the curable component preferably has an average of at least two silicon-bonded unsaturation functional groups per molecule. Such unsaturation functional groups are preferably carbon-carbon unsaturated groups or radicals, more preferably groups or radicals which include a carbon-carbon double bond and still more preferably vinyl groups. The number of unsaturation functional groups can vary from two per molecule. For example, component (A) can be a blend of two or more polyorganosiloxanes in which some molecules may have more unsaturation functional groups than two per molecule and some may have less than two per molecule. Although it is not required that the silicon-bonded unsaturation functional groups be located in the alpha, omega (or terminal) positions of the polyorganosiloxanes, it is preferred that at least some of these groups be located in these positions. The unsaturation functional groups are preferably located at the polymer ends because such polyorganosiloxanes are economical to prepare and provide satisfactory products. However, because of the polymeric nature of component (A), its preparation may result in products which have some variations in structure, and some unsaturation functional groups may not be in the terminal positions even if the intent is to have them in these positions. Thus, the resulting polyorganosiloxanes may have a portion of the unsaturation functional groups located at branch sites.

The polyorganosiloxanes of component (A) are preferably essentially linear polymers which can have some branching. The polyorganosiloxanes may have silicon-oxygen-silicon backbones with an average of greater than two organo groups per silicon atom. Preferably, component (A) is made up of diorganosiloxane units with triorganosiloxane units for end groups, but small amounts of monoorganosiloxane units and $SiO_2$ units may also be present. The organo radicals preferably have less than about 10 carbon atoms per radical and are each independently selected from monovalent hydrocarbon radicals such as methyl, ethyl, vinyl, propyl, hexyl and phenyl and monovalent substituted hydrocarbon radicals, such as the perfluoroalkylethyl radicals. Examples of component (A) include dimethylvinylsiloxy endblocked polydimethylsiloxane, methylphenylvinylsiloxy endblocked polydimethylsiloxane, dimethylvinylsiloxy endblocked polymethyl-(3,3,3-trifluoropropyl)siloxane, dimethylvinylsiloxy endblocked polydiorganosiloxane copolymers of dimethylsiloxane units and methylphenylsiloxane units, and methylphenylvinylsiloxy endblocked polydiorganosiloxane copolymers of dimethylsiloxane units and diphenylsiloxane units, and the like. The polyorganosiloxanes can have siloxane units such as dimethylsiloxane units, methylphenylsiloxane units, diphenylsiloxane units, methyl-(3,3,3-trifluoropropyl)siloxane units, monomethylsiloxane units, monophenylsiloxane units, dimethylvinylsiloxane units, trimethylsiloxane units, methylphenylvinylsiloxane units, and $SiO_2$ units. Polyorganosiloxanes of component (A) can be single polymers or mixtures of polymers. These polymers preferably have at least about 50 percent of the organic radicals as methyl radicals. Many polyorganosiloxanes useful as component (A) are well known in the art. A preferred component (A) is a polydimethylsiloxane endblocked with dimethylvinylsiloxy units or methylphenylvinylsiloxy units. In one embodiment, component (A) has a viscosity of about 100 to less than about 1000 or about 2000 or about 5000, for example, to about 800, centipoise.

Component (B) of the present curable components includes organosilicon compounds containing at least 2, and preferably at least 3, silicon-bonded hydride groups, i.e., hydrogen atoms, per molecule. Each of the silicon-bonded hydride groups is preferably bonded to a different silicon atom. The remaining valences of the silicon atoms are satisfied by divalent oxygen atoms or by monovalent radicals, such as alkyl having 1 to about 6 carbon atoms per radical, for example, methyl, ethyl, propyl, isopropyl, butyl, tertiary butyl, pentyl, hexyl, cyclohexyl, substituted alkyl radicals, aryl radicals, substituted aryl radicals and the like. The silicon-bonded hydride group containing organosilicon compounds can be homopolymers, copolymers and mixtures thereof which contain siloxane units of the following types:

$RSiO_{1.5}$, $R_2SiO$, $R_3SiO_{0.5}$, $RHSiO$, $HSiO_{1.5}$, $R_2HSiO_{0.5}$, $H_2SiO$, $RH_2SiO_{0.5}$ and $SiO$ where R is the monovalent radical, for example, as defined above. Examples include polymethylhydrogensiloxane cyclics, copolymers of trimethylsiloxy and methylhydrogensiloxane, copolymers of dimethylhydrogensiloxy and methylhydrogensiloxane, copolymers of trimethylsiloxy, dimethylsiloxane and methylhydrogensiloxane, copolymers of dimethylhydrogensiloxane, dimethylsiloxane and methylhydrogensiloxane and the like. In one embodiment, component B has a viscosity of about 100 to less than about 1000 or about 2000 or about 5000, for example, to about 800, centipoise.

The platinum group metal catalyst component, component (C), can be any of the compatible platinum group metal-containing catalysts known to catalyze the addition of silicon-bonded hydrogen atoms (hydride groups) to silicon-bonded vinyl radicals.. Platinum group metal-containing catalysts can be any of the known forms which are compatible such as, platinic chloride, salts of platinum, chloroplatinic acid and various complexes. The platinum group metal-containing catalyst component, can be used in any catalytic quantity, such as in an amount sufficient to provide at least about 0.1 ppm weight of platinum group metal (calculated as elemental metal) based on the combined weight of component (A) and component (B). Preferably at least about 10 ppm, for example, at least about 20 ppm or at least 30 ppm or at least about 40 ppm, by weight of platinum group metal, based on the combined weight of component (A) and component (B), is used. In one useful embodiment, the platinum group metal-containing component is chloroplatinic acid, preferably complexed with a siloxane such as tetramethylvinylcyclosiloxane (i.e. 1,3,5,7-tetramethyl-1,3,5,7-tetravinylcyclosiloxane).

The polymer component is substantially nonfunctional, that is such component does not substantially participate in the polymerization, for example, cross-linking such as hydrosilylation, reaction or reactions of the curable component. This polymer component has a viscosity which is greater than the viscosity of the curable component. Preferably, the polymer component has a higher molecular weight than does the curable component.

Although any suitable type of polymer may be included in the present polymer components, it is preferred that the polymer component be made up of one or more silicone polymers. Such polymers are preferably compatible with the cross-linked polymer material formed by the polymerization of the curable component. The polymer component is preferably present in the mixture in an amount effective to increase the viscosity, more preferably by at least about 5 times and still more preferably by at least about 1 order of magnitude, of the mixture relative to a substantially identical mixture without the polymer component. The polymer component preferably has a viscosity of at least about 50,000 centipoise, more preferably at least about 75,000 centipoise.

A particularly useful polymer component includes one or more substantially non-functional polyorganosiloxane components having the desired viscosity and/or molecular weight. Such substantially non-functional polyorganosiloxane components can be generally described with reference to component (A) of the curable component except that non-functional groups are substituted for the unsaturation functional groups of component (A), and the molecular weight of the substantially non-functional polyorganosiloxane component is increased relative to component (A). An especially useful polymer component includes one or more polyalkylsiloxanes, more preferably polymethylsiloxanes. At least a portion of the alkyl groups can be replaced by aryl, preferably phenyl, groups.

The mixture containing both the polymerizable component and the polymer component preferably has a viscosity of at least about 5,000 or about 10,000 or about 18,000 centipoise. Mixture viscosities in excess of about 50,000 centipoise are preferably avoided so as to avoid injection difficulty.

The relative proportions of (A) and (B) in the curable component and of the curable component and polymer component in the mixture can be varied over a wide range, for example, to obtain desired injection and other processing advantages and to produce final products with desired properties. The relative weight proportion of (A) and (B) in the curable component preferably is in the range of about 10:1 to about 1:10. The relative weight proportion of the curable component to the polymer component preferably is in the range of about 3:1 to about 1:3, more preferably about 2:1 to about 1:2.

A reinforcer component may be dispersed in the final polymer mixture. When an injectable IOL is to be provided, it is preferred that no such reinforcer component be included. In accordance with one embodiment of the invention, the reinforcer component may be used in a ratio of about 15 to about 45 parts by weight of the reinforcer component to 100 parts of the total composition containing the final mixture.

Silica, for example, fumed silica, and organic resins are very useful as the reinforcer component. Fumed silica itself is commercially available. Processes for trimethylsilylating the surface of fumed silica for the purpose of rendering the silica surface hydrophobic and more compatible with component (A) of the curable component are also known and within the skill of the art. A number of organic resins are known to be useful for reinforcing articles which include cross-linked silicone polymers or silicone elastomers. Of course, the reinforcer component used in the present compositions employed in optical applications should be optically clear or at least have no significant detrimental effect on the optical clarity of the final product. The refractive index of the reinforcer component is preferably at least about equal to or greater than the refractive index of the polymer mixture.

The fumed silica reinforcer useful in the present compositions may have a surface area of about 100 to about 450 meters$^2$/gram.

In the preparation of the present compositions, component (A) of the curable component may be intimately mixed with a reinforcer component. The intimate mixing is preferably aided by treating the mixture on a roll mill or like device.

Component (A), with or without and reinforcer component, is hereinafter referred to as the "base". The base preferably has a suitable optical refractive index and a relatively low viscosity, preferably less than about 2000 or about 5000 centipoise and more preferably less than about 1000 centipoise. Component (B) preferably has a viscosity of less than about 2000 or about 5000 centipoise, more preferably less than about 1000 centipoise.

Preparation of the uncured base for cross-linking may be accomplished as follows. The base is divided into two aliquots which preferably are of equal weight. The aliquots are termed "Part A" and "Part B" or first and second aliquot parts. The silicon-bonded unsaturation functional groups of component (A) are present in both the first and second aliquots of the base.

Component (B) is added to the second aliquot (Part B).

Alternately, all of component (A) is placed in Part A, and all of component (B) is placed in Part B.

The platinum group metal, preferably platinum-containing catalyst, component (C), may be added to the first aliquot (Part A).

The polymer component may be included in either or both of the first and second aliquots, or may be initially combined with the mixed first and second aliquots.

After mixing of the aliquots (Part A and Part B) (and the polymer component), the cross-linking preferably should not proceed too rapidly at room temperature. For example, if an injectable IOL is to be produced, the mixture should be such that work times at room temperature of at least about 1 minute, preferably about 2 minutes to about 10 or about 20 minutes, are provided. If the cross-linking is to occur outside the constraints of the eye, the mixture should be such that work times at room temperature of at least about 2, preferably at least about 4 or about 6, hours are provided. A suitable cross-linking inhibitor, such as 1, 2, 3, 4 tetramethyl- 1,2,3,4-tetravinyl cyclotetrasiloxane, may be added to the second aliquot (Part B). The cross-linking inhibitor may be added to the second aliquot in an amount in the range of about 0.01 to about 0.2 parts per hundred by weight. If the mixture is to be cured in the eye, for example, into an injectable IOL, it is preferably free of cross-linking inhibitor.

An ultraviolet light absorbing material, preferably a polymerizable ultraviolet light absorbing material, may be mixed into the second aliquot.

The ultraviolet light absorbing material, for example, selected from vinyl functional 2-hydroxybenzophenones and vinyl functional benzotrizoles, is preferably covalently linked to the silicone elastomer of the elastomeric composition during the cross linking step. More preferably, the ultraviolet absorbing material is 2(2'-hydroxy-3'-t-butyl-5'vinyl-phenyl)-5-chloro-2H-benzotriazole. The ultraviolet light absorbing material is preferably added to the second aliquot in an amount in the range of about 0.1% to about 1% or about 5% by weight.

The curing or cross-linking occurs at conditions effective to provide the desired polymer mixture. Curing temperatures may vary, for example, from about 20° C. to about 200° C., and curing times may range, for example, from about 1 minute to about 5 hours or about 10 hours or more.

When the precursor composition or mixture is to be introduced or injected into the eye, the curing temperature is the physiological temperature in the eye, for example, for humans in the range of about 350° C. to about 370° C. Lack of mobility of the injected composition preferably occurs within about 20 minutes, more preferably within about 10 minutes, of injection. Final cure preferably occurs within about 6 hours, more preferably within about 2 hours, of injection.

Formation of IOL bodies or optics from the polymer mixtures of the present invention may be accomplished by liquid injection molding or by cast or compression molding or other types of molding of the intimately mixed first and second aliquots. Although these processes are well known in the art they are briefly summarized as follows.

In the liquid injection molding process the mixed aliquots are injected into a hot mold kept at about 1200° C. to about 150° C. The cross-linking or curing process may then be completed in about five minutes.

In the cast or compression molding process, the mixed aliquots are placed into appropriate molds, and the molds are thereafter positioned in an oven heated to about 1200° C. to about 180° C. Under these conditions the cure is completed in about 1 to about 30 minutes. The cast molding process can also be completed at room temperature in significantly longer time periods.

The IOLs made in accordance with the present invention have the above-described advantageous optical and mechanical properties.

The following non-limiting examples illustrate certain aspects of the present invention.

EXAMPLE 1

A two part, i.e., Part A and Part B, siloxane precursor system for addition-cure cross-linked polysiloxane polymer compositions was selected for testing. This commercially available system is sold by General Electric Company under the trademark GE 6196.

Part A was a vinyl-containing polydimethylsiloxane and had a viscosity of about 750 centipoise. Part A also included about 34 ppm by weight of a platinum-containing catalyst, calculated as elemental platinum.

Part B was a polysiloxane including both silicon-bonded methyl groups and silicon-bonded hydride groups. Part B had a viscosity of about 750 centipoise.

A trimethyl-terminated polydimethysiloxane (PDMS) was also selected for testing. This material, sold by McGhan NuSil under the trademark S-7200, had a viscosity of 100,000 centipoise.

Two separate precursor portions were prepared by blending the following components together:

| PORTION 1 | | PORTION 2 | |
|---|---|---|---|
| Part A | 50 wt. % | Part B | 67 wt. % |
| PDMS | 50 wt. % | PDMS | 33 wt. % |

Portion 1 and Portion 2 were combined in a weight ratio of 1:1. This combination, which had a viscosity of about 20,000 centipoise, was placed in a viscometer at 370° C. Cross-linking of Part A and Part B occurred so that a maximum viscosity was obtained in less than 10 minutes.

The resulting polymer mixture did not run (that is, was not fluidic) at room temperature and demonstrated good resiliency.

EXAMPLE 2

Example 1 was repeated except that Portion 1 and Portion 2 were:

| PORTION 1 | | PORTION 2 | |
|---|---|---|---|
| Part A | 25 wt. % | Part B | 50 wt. % |
| PDMS | 75 wt. % | PDMS | 50 wt. % |

Portion 1 and Portion 2 were combined in a weight ratio of 1:1. This combination, which had a viscosity estimated to be 1000 to 10,000 centipoise greater than the viscosity of the combination of Example 1, was placed in a viscometer at 37° C. Cross-linking of Part A and Part B occurred so that a maximum viscosity was obtained in less than 10 minutes.

This polymer mixture had a higher cross-link density than did the polymer mixture of Example 1.

EXAMPLE 3

The precursor mixture used in Example 1 is injected into an evacuated lens capsule of a human eye. Over a period of time, the mixture cures into an optically clear polymeric composition. Satisfactory results are obtained in terms of continued optical clarity of the cured material over a prolonged period of time, for example, in the range of about one month to about 6 months or a year after injection.

EXAMPLE 4

The precursor mixture used in Example 2 is injected into an evacuated lens capsule of a human eye. Over a period of time, the mixture cures into an optically clear polymeric composition. Satisfactory results are obtained in terms of continued optical clarity of the cured material over a prolonged period of time, for example, in the range of about one month to about 6 months or a year after injection.

While this invention has been described with respect to various specific examples and embodiments, it is to be understood that the invention is not limited thereto and that it can be variously practiced within the scope of the following claims.

What is claimed is:

1. An intraocular lens optic comprising a polymer mixture which is optically clear and is derived from polymerization of the curable component in a mixture comprising:
   a curable component comprising (A) an unsaturation functional polyorganosiloxane component, (B) an organosilicon component including silicon-bonded hydride groups which react with the functional unsaturated groups included in (A) during said polymerization, and (C) an effective amount of a platinum group metal-containing catalyst component; and
   a silicone polymer component which is substantially nonfunctional, provided that the viscosity of said silicone polymer component is greater than about 50,000 centipoise and is greater than the viscosity of said curable component, said silicone polymer component being present in an amount effective to increase the viscosity of said mixture relative to the viscosity of a substantially identical mixture without said silicone polymer component.

2. The intraocular lens optic of claim 1 wherein the viscosity of said silicone polymer component is at least about 50 times greater than the viscosity of said curable component.

3. The intraocular lens optic of claim 1 wherein the viscosity of said curable component is less than bout 1,000 centipoise.

4. The intraocular lens optic of claim 1 wherein said curable component has a chemical make-up and is present in an amount effective to form cross-linked polymer material upon said polymerization with sufficient cross-link density so that said optic is soft and resilient.

5. The intraocular lens optic of claim 1 wherein said curable component is present in an amount effective to form cross-linked polymer material upon said polymerization with sufficient cross-link density to effectively immobilize at least a portion of said polymer component.

6. The intraocular lens optic of claim 1 wherein said curable component is present in an amount effective to form cross-linked polymer material upon said polymerization, which cross-linked polymer material effectively immobilizes at least a major portion of said silicone polymer component.

7. The intraocular lens optic of claim 1 wherein said silicone polymer component is present in an amount effective to increase the viscosity of said mixture by at least about 1 order of magnitude relative to the viscosity of a substantially identical mixture without said silicone polymer component.

8. The intraocular lens of claim 1 wherein said unsaturation functional polyorganosiloxane component includes a vinyl-containing polyorganosiloxane, and said silicone polymer component is a polyalkylsiloxane polymer.

9. The intraocular lens optic of claim 1 wherein said silicone polymer component comprises a polyorganosiloxane polymer.

10. A method of forming an intraocular lens comprising:
    forming a mixture of a curable component comprising (A) an unsaturation functional polyorganosiloxane component, (B) an organosilicon component including silicon-bonded hydride groups which react with the functional unsaturated groups included in (A) during polymerization of said curable component, and (C) an effective amount of a platinum group metal-containing catalyst component, and a silicone polymer component which is substantially non-functional, provided that the viscosity of said silicone polymer component is at least about 50 times greater than the viscosity of said curable component said silicone polymer component being present in an amount effective to increase the viscosity of said mixture relative to the viscosity of a substantially identical mixture without said silicone polymer component; and
    subjecting said mixture to conditions effective to polymerize said curable component, and said subjecting results in forming a cross-linked polymer material from said curable component.

11. The method of claim 10 wherein said silicone polymer component is a polyorganosiloxane polymer.

12. The method of claim 10 wherein said mixture is injected into the lens capsule of an eye and said conditions are present in said eye.

13. The method of claim 10 wherein the viscosity of said curable component is less than about 1000 centipoise.

14. The method of claim 10 wherein said curable component has a chemical make-up and is present in an amount effective to form cross-linked polymer material upon said polymerization with sufficient cross-link density so that said intraocular lens is soft and resilient.

15. The method of claim 10 wherein said cross-linked polymer material has sufficient cross-link density so that said cross-linked polymer material effectively immobilizes at least in major portion of said polymer component.

* * * * *

UNITED STATES PATENT AND TRADEMARK OFFICE
CERTIFICATE OF CORRECTION

PATENT NO. : 5,391,590

DATED : February 21, 1995

INVENTOR(S) : Gerace et al

It is certified that error appears in the above-indentified patent and that said Letters Patent is hereby corrected as shown below:

Column 10, line 10; after "said" insert --silicone--.

Column 10, line 21; delete "without-said" and insert in place thereof --without said--.

Column 8, lines 7 and 8; delete "about 350°C. to about 370°C." and insert in place thereof --about 35°C to about 37°C--

Column 8, line 27; delete "heated to about 1200°C." and insert in place thereof --heated to about 120°C--.

Column 8, line 64; delete "370°C." and insert in place thereof --37°C--.

Signed and Sealed this

Tenth Day of December, 1996

Attest:

BRUCE LEHMAN

*Attesting Officer*   *Commissioner of Patents and Trademarks*